US008467980B2

(12) United States Patent
Campbell et al.

(10) Patent No.: US 8,467,980 B2
(45) Date of Patent: Jun. 18, 2013

(54) CALCULATING INSULIN ON BOARD FOR AN EXTENDED BOLUS BEING DELIVERED BY AN INSULIN DELIVERY DEVICE

(75) Inventors: Robert Campbell, Waltham, MA (US); Amanda Abramovich, Arlington, MA (US)

(73) Assignee: Insulet Corporation, Bedford, MA (US)

( * ) Notice: Subject to any disclaimer, the term of this patent is extended or adjusted under 35 U.S.C. 154(b) by 0 days.

(21) Appl. No.: 13/399,279

(22) Filed: Feb. 17, 2012

(65) Prior Publication Data

US 2012/0150144 A1    Jun. 14, 2012

Related U.S. Application Data

(62) Division of application No. 12/175,970, filed on Jul. 18, 2008, now Pat. No. 8,140,275.

(51) Int. Cl.
*G01F 17/00*    (2006.01)

(52) U.S. Cl.
USPC .......................................................... 702/50

(58) Field of Classification Search
USPC .......................................................... 702/50
See application file for complete search history.

(56) References Cited

U.S. PATENT DOCUMENTS

2008/0172028 A1\* 7/2008 Blomquist ..................... 604/500
2010/0298765 A1\* 11/2010 Budiman et al. ................ 604/66

\* cited by examiner

*Primary Examiner* — Aditya Bhat
(74) *Attorney, Agent, or Firm* — Grossman Tucker Perreault & Pfleger, PLLC (57) ABSTRACT

A system and method may be used to calculate insulin on board (IOB) for an extended bolus being delivered by an insulin infusion pump. In general, the system and method calculates an extended bolus IOB value for the extended bolus, which takes into account the insulin currently on board from the extended bolus and the insulin scheduled to be delivered by the extended bolus over a subsequent time period equivalent to a duration of insulin action. The extended bolus IOB value may be used to calculate a suggested bolus.

20 Claims, 4 Drawing Sheets

CALCULATING INSULIN ON BOARD FOR AN EXTENDED BOLUS BEING DELIVERED BY AN INSULIN DELIVERY DEVICE

CROSS-REFERENCE TO RELATED APPLICATIONS

This application is a divisional of U.S. patent application Ser. No. 12/175,970 filed Jul. 18, 2008, now U.S. Pat. No. 8,140,275, which is fully incorporated herein by reference.

TECHNICAL FIELD

The present invention relates to insulin delivery systems and methods that deliver insulin to a patient and more particularly, to a system and method for calculating insulin on board for an extended bolus being delivered by an insulin delivery device.

BACKGROUND INFORMATION

With advances in technology, medical devices are capable of significantly improving the treatment and/or management of various diseases or illnesses. One such medical device is an insulin delivery system capable of delivering insulin to a diabetic individual and managing the delivery of insulin. One example of an insulin delivery system includes an insulin delivery device or infusion pump that is secured to the user to deliver the insulin and a wireless, hand-held device that communicates with the delivery device to control and manage insulin delivery. The hand-held device may program the infusion pump with personalized insulin delivery instructions and monitor the operation of the infusion pump, thereby facilitating the management of diabetes. The insulin infusion pump may deliver insulin according to a delivery program that provides different doses of insulin at different times of day, for example, a basal program that provides different basal rates over different time segments. The insulin infusion pump may also deliver bolus doses of insulin, for example, to correct for high blood glucose or in connection with an event, such as a meal, that is likely to affect blood glucose. Extended bolus doses may be delivered, for example, over an extended period of time to avoid a high initial dose of insulin and to allow extended insulin action.

Existing insulin delivery systems may calculate appropriate amounts of insulin to be delivered based on a number of factors. Insulin delivery systems may calculate an appropriate bolus dose based on, for example, a blood glucose level and an expected carbohydrate intake. Another factor that may be considered when determining an appropriate bolus dose is insulin on board (IOB). Because insulin takes time to be processed in the body, residual insulin often remains in the body for a period of time after receiving the insulin and keeps working after the carbohydrates have been processed. To avoid delivering a bolus dose that would result in too much insulin (e.g., insulin stacking), the IOB may be subtracted from a bolus dose that would otherwise be appropriate (e.g., for a given blood glucose level and carbohydrate intake). Because insulin is delivered over an extended period of time during an extended bolus, factoring in the IOB during such extended boluses is more difficult.

BRIEF DESCRIPTION OF THE DRAWINGS

These and other features and advantages will be better understood by reading the following detailed description, taken together with the drawings wherein.

DETAILED DESCRIPTION

An insulin on board (IOB) calculation system and method, consistent with embodiments described herein, may be used to calculate insulin on board for an extended bolus being delivered by an insulin infusion pump. In general, the system and method calculates an extended bolus IOB value for the extended bolus, which takes into account the insulin currently on board from the extended bolus and the insulin scheduled to be delivered by the extended bolus over a subsequent time period equivalent to a duration of insulin action. The extended bolus IOB value may be used to calculate a suggested bolus and/or to provide insulin on board information to the user for other purposes.

As used herein, "insulin on board" generally refers to insulin that is in the body effectively lowering blood glucose. As described in greater detail below, "insulin on board" may include insulin that is currently in the body at a particular time and/or insulin that will be in the body during a period of time in the future.

As used herein, "extended bolus" refers to an infusion of a predetermined amount of insulin that includes at least a portion extended over a period of time instead of being delivered immediately. In an embodiment, the period of time of an extended bolus may be at least 30 minutes. An extended bolus may include a bolus in which a portion of the insulin is delivered immediately and a portion of the insulin is delivered over the extended period of time. An extended bolus or the extended portion of an extended bolus is generally provided to cover carbohydrate intake (i.e., a meal bolus), although at least a portion of an extended bolus may also be provided to correct a high blood glucose level (i.e., a correction bolus). The duration of time of an extended bolus may vary depending upon various factors such as the nature of the food for which the bolus is being taken (e.g., high fat high protein foods may raise blood sugar for an extended time) and/or the person receiving the insulin (e.g., the ability to digest).

As used herein, "duration of insulin action" refers to the amount of time during which insulin effectively lowers blood glucose. Duration of insulin action may be specific to the person receiving the insulin and may be a user-specified value. Currently available rapid/short acting insulin, for example, may have a duration of insulin action between about 3-5 hours. As used herein, a time period "substantially equal to" the duration of insulin action refers to a time period that is either the same as the duration of insulin action or that varies from the duration of insulin action by some relatively small amount that is not likely to have a significant impact on the user when calculating IOB values and/or suggested boluses as described herein.

As used herein, "suggested bolus" refers to a bolus that is determined to be appropriate for a user at a particular time and may be based on an amount of insulin that will cover the anticipated increase in blood glucose from a carbohydrate intake and/or an amount of insulin that will reduce a blood glucose level to within a target blood glucose range. A suggested bolus may include meal bolus and correction bolus components. A "meal bolus" refers to a bolus that is based on an amount of insulin that will cover a carbohydrate intake. A "meal bolus" is not limited to a meal per se and may be associated with any form of carbohydrate intake. A "correction bolus" refers to a bolus that is based on an amount of insulin that will reduce a blood glucose level to within a target blood glucose range.

Figure 1:
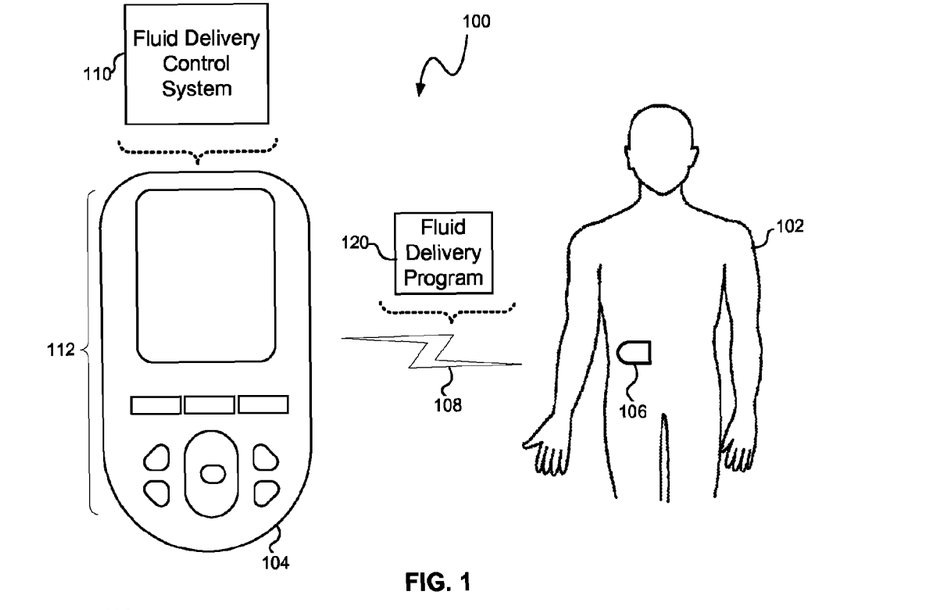
FIG. 1 is a diagrammatic view of an insulin delivery system, consistent with one embodiment of the present invention.

Referring to FIG. 1, an IOB calculation system and method, consistent with embodiments of the present invention, may be implemented in an insulin delivery system 100 used by a user or patient 102. One embodiment of the fluid delivery system 100 may include a hand-held delivery management device 104 and an infusion pump 106 worn by the patient 102. In the exemplary embodiments, the delivery management device 104 communicates with the infusion pump 106, for example, over a wireless communication link 108, to program and monitor the infusion pump 106 and to manage delivery of a fluid, such as insulin, to a patient according to a treatment regimen. One example of such a management device 104 and infusion pump 106 is the OmniPod® insulin management system available from Insulet Corporation. The IOB calculation system and method may also be used with a fluid delivery system in which the management device and the infusion pump are integrated as a programmable infusion pump. Those skilled in the art will recognize that the IOB calculation system and method, described in greater detail below, may be used in any type of insulin delivery system or fluid delivery system.

According to the exemplary embodiment, the delivery management device 104 may include a fluid delivery control system 110 for controlling delivery of the fluid, for example, by programming the infusion pump 106 with personalized delivery instructions that specify certain doses at certain times of day. The fluid delivery control system 110 may include hardware, software, firmware or any combination thereof to perform the fluid delivery control functions. The delivery management device 104 may also include user interface components 112, such as a visual display, audio devices, and electromechanical switches, for allowing a user to receive and provide information. The delivery management device 104 may further include transmitter and receiver components (not shown), such as a wireless transceiver, for communicating with the infusion pump 106 using radio frequency or other wireless communication standards and protocols. One example of the insulin delivery system, and particularly the user interface, is disclosed in greater detail in U.S. patent application Ser. No. 10/827,582 filed on Apr. 19, 2004 (U.S. Patent Application Publication No. 2005/0022274), which is commonly owned with the present application and fully incorporated herein by reference.

According to the exemplary embodiment, the infusion pump 106 may include fluid delivery components (not shown), such as a dispenser assembly for causing fluid from a fluid reservoir to flow through a flow path assembly to a transcutaneous access tool (e.g., a needle) for infusion to a patient. The infusion pump 106 may also include one or more memory units and one or more processor units (not shown) that are capable of storing and executing the instructions provide by the delivery management device 104. The infusion pump 106 may further include a system clock (not shown) that keeps the time of day (referred to as the program time) to determine when certain programmed doses of fluid should be delivered. The infusion pump 106 may also include transmitter and receiver components (not shown), such as a wireless transceiver, for communicating with the delivery management device 104.

In general, the delivery management device 104 is used to remotely initialize and program the infusion pump 106 with a patient's custom fluid delivery profile. The delivery management device 104 may set the system clock (or program time) of the infusion pump 106 to correspond to the local time on the delivery management device 104. The fluid delivery control system 110 may also generate or establish one or more fluid delivery programs 120 to be transmitted to the infusion pump 106, for example, over the wireless communication link 108. Fluid delivery programs may include, but are not limited to, basal programs, temporary basal rates, and/or bolus doses. In a basal program, for example, the different doses of fluid may be different basal rates of fluid delivered over basal rate time segments. Bolus doses may include, for example, meal boluses and/or correction boluses. The infusion pump 106 may provide bolus doses immediately (i.e., immediate boluses) and/or over an extended period of time defined by the fluid delivery program (i.e., extended boluses). The fluid delivery program 120 may include instructions that, when executed by the infusion pump 106, cause the infusion pump 106 to provide the specified doses at the specified times.

The infusion pump 106 may operate according to the fluid delivery program(s) 120 on the infusion pump 106 independently of the delivery management device 104, for example, until the fluid delivery control system 110 on the delivery management device 104 alters or stops the fluid delivery program and/or provides a new fluid delivery program. The delivery management device 104 may also be used to check the status of the infusion pump 106 and/or the active delivery program, to cause the infusion pump 106 to deliver additional doses (e.g., temporary basal rates or bolus doses), to suspend delivery and/or to modify the fluid delivery program(s).

The delivery management device 104 may also be used to determine a suggested bolus based on various factors including, without limitation, insulin on board (IOB), duration of insulin action, insulin-to-carbohydrate (I/C) ratios, insulin correction factors, blood glucose levels and carbohydrate intake. When extended boluses are running, for example, the delivery management device 104 may calculate an extended bolus IOB value taking into consideration the actual insulin on board and insulin to be delivered in a subsequent time period equivalent to the duration of insulin action.

Figure 2:
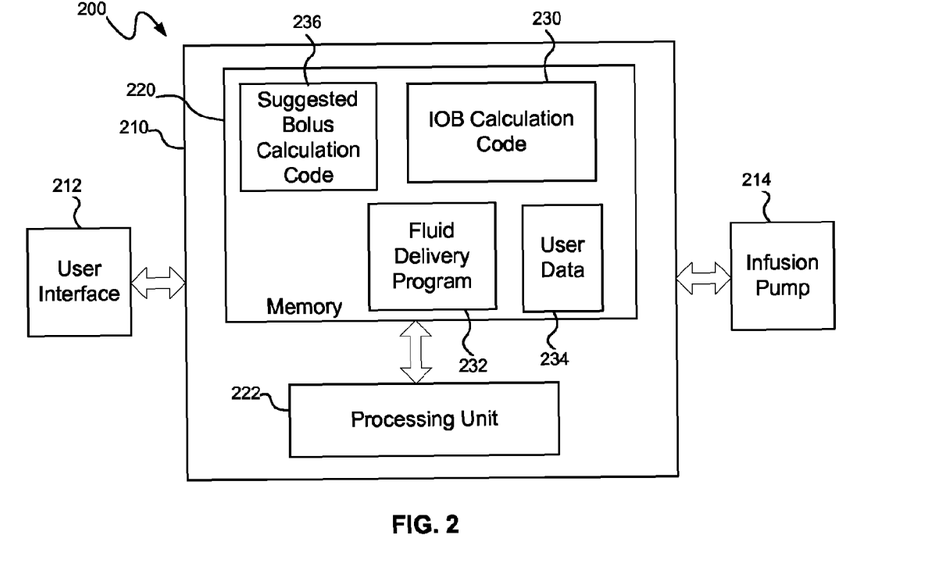
FIG. 2 is a diagrammatic view of an insulin delivery system including one embodiment of a system for calculating insulin on board and for calculating a suggested bolus.

As shown in FIG. 2, one embodiment of an IOB calculation system may be implemented as software on a fluid delivery system 200. The fluid delivery system 200 may include fluid delivery control system 210, user interface 212 coupled to the fluid delivery control system 210, and infusion pump 214 coupled to the fluid delivery control system 210. In one embodiment, the fluid delivery control system 210 and user interface 212 may be implemented on a hand-held delivery management device (e.g., as shown in FIG. 1) separate from the infusion pump 206. The fluid delivery control system 210, user interface 212 and the infusion pump 214 may also be integrated into a single programmable pump device. The fluid delivery control system 210 may include one or more memory units 220 and one or more processing units 222 for storing and executing the IOB calculation software and other software such as suggested bolus calculation software.

The fluid delivery control system 210 may include IOB calculation code 230 including a series of instructions that, when executed by the processing unit 222, embody all or part of the functionality described herein with respect to the IOB calculation system and method. The fluid delivery control system 210 may also include suggested bolus calculation code 236 including a series of instructions that, when executed by the processing unit 222, embody all or part of the functionality described herein with respect to calculating suggested bolus doses.

The fluid delivery control system 210 may also include fluid delivery program data 232 and/or user data 234 used to calculate the insulin on board and/or the suggested bolus. The fluid delivery program data 232 may include data defining the specified delivery doses (e.g., bolus doses) and the specified durations and/or times (e.g., duration of an extended bolus) of doses being delivered according to one or more fluid delivery programs. In one example, the fluid delivery program data 232 may include dose amounts for each of a plurality of time segments over a 24 hour day (e.g., bolus amounts for half hour time segments). For an extended bolus, the fluid delivery program data 232 may also include data representing an amount already delivered (i.e., a completed portion), an amount remaining to be delivered (i.e., a scheduled portion), a time elapsed and a time remaining. The user data 234 may include data specific to the user such as duration of insulin action, blood glucose levels, insulin-to-carbohydrate (I/C) ratios, correction factors and carbohydrate intake amounts. The user data 234 may also include insulin delivery history data representing insulin delivered to the user over a previous period of time (e.g., previous completed boluses) and calculated IOB values.

Those skilled in the art will recognize that the IOB calculation software and suggested bolus calculation software may be created using various formats and programming languages. Although the exemplary embodiment is described and shown as one software implementation of the IOB calculation system and method, those skilled in the art will recognize that alternative embodiments may be implemented using any type of circuitry or logic, such as pre-programmed hardware elements or as a combination of hardware, software and/or firmware.

Figure 3:
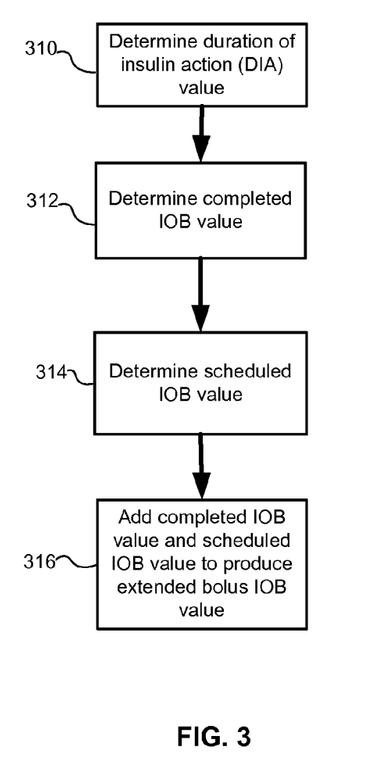
FIG. 3 is a flow chart illustrating one method of calculating insulin on board for an extended bolus, consistent with an embodiment of the present invention.

Referring to FIG. 3, one method of calculating insulin on board for an extended bolus that is currently running is shown and described. In one embodiment, the extended bolus is a meal bolus that was initiated to cover an anticipated increase in blood glucose level as a result of a carbohydrate intake. The method includes determining 310 a duration of insulin action (DIA) value to be used in the IOB calculation. The duration of insulin action may be determined, for example, by retrieving a stored DIA value or by receiving a DIA value input by the user.

The method includes determining 312 a completed IOB value representing an amount of insulin on board from a completed portion of the extended bolus, which has been completed within a previous time period substantially equal to the duration of insulin action. The completed portion of the extended bolus may be represented by a series of immediate bolus portions delivered at different times during the previous time period. For an extended bolus of 6 units delivered over an extended period of 6 hours, for example, the extended bolus may be represented by a series of twelve 0.5 unit immediate bolus portions delivered every ½ hour and the completed portion after 2 hours may be represented as a series of four 0.5 unit immediate bolus portions delivered every ½ hour. The completed IOB value may thus be determined by calculating IOB values for each of the immediate bolus portions at the respective times and adding the calculated IOB values for the series of immediate bolus portions within the previous time period.

According to one example, each of the calculated IOB values for an immediate bolus portion of a completed portion of an extended bolus may be calculated as follows:

$$IOB = (V \times (1 - T_e/DIA)) \qquad (1)$$

where V is the volume of the immediate bolus portion that was delivered, DIA is the duration of insulin action, and $T_e$ is the elapsed time since the immediate bolus portion was delivered. The IOB value for the completed portion of the extended bolus may then be calculated as the sum of the IOB values calculated for each of the immediate bolus portions as follows:

$$IOB_c = IOB_1 + \ldots IOB_n \qquad (2)$$

where n is the number of immediate bolus portions in the completed portion of the extended bolus within the previous time period substantially equal to the duration of insulin action. Other methods for calculating the completed IOB value may also be used.

The method also includes determining 314 a scheduled IOB value representing an amount of insulin scheduled to be delivered during a scheduled portion of the extended bolus and within a subsequent time period substantially equal to the duration of insulin action. The scheduled IOB value may be calculated based on the extended bolus amount, the time remaining for the extended bolus, and the duration of insulin action. According to one example, the schedule IOB ($IOB_s$) is calculated as follows:

$$IOB_s = V_t \times (T_s/D) \qquad (3)$$

where $V_t$ is the total volume of the extended bolus, $T_s$ is the time for delivering the schedule portion of the extended bolus, and D is the duration of the extended bolus. The duration of the extended bolus may be longer or shorter than the duration of insulin action. If the time remaining in the extended bolus is more than the DIA, the time $T_s$ for delivering the scheduled portion is the DIA value. If the time remaining is less than the DIA, the time $T_s$ for delivering the scheduled portion is time remaining in the extended bolus. Other methods for calculating the scheduled IOB value may also be used.

The extended bolus IOB value may then be obtained 316 by adding the completed IOB value and the scheduled IOB value, for example, as follows:

$$IOB_e = IOB_c + IOB_s \qquad (4)$$

The extended bolus IOB value may then be stored, displayed to the user and/or used in other calculations such as a suggested bolus calculation.

Figure 4:
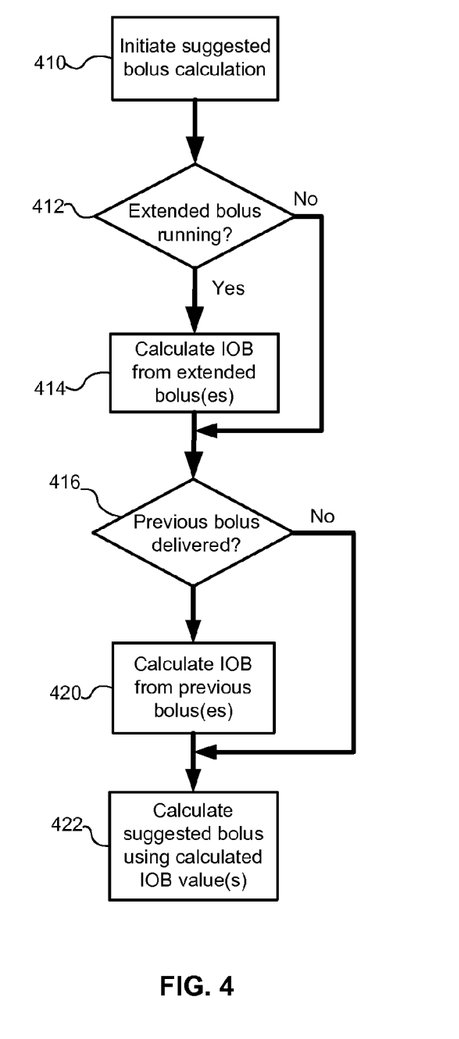
FIG. 4 is a flow chart illustrating one method of calculating a suggested bolus using an extended bolus IOB value, consistent with an embodiment of the present invention.

FIG. 4 shows one method of calculating a suggested bolus, which takes into account an extended bolus IOB value. The method may initiate 410 a suggested bolus calculation, for example, automatically or in response to a user requesting a suggested bolus. To obtain insulin on board information to be used in the suggested bolus calculation, the method may calculate IOB values for an extended bolus that is currently running and/or for a previous bolus that was completed. After the IOB calculation is initiated, for example, the method may determine 412 if an extended bolus is running. If an extended bolus is running, the system may calculate 414 the insulin on board value(s) from the currently running extended bolus(es), for example, using the method described above.

The system may also determine 416 if any previous boluses have been delivered within a previous time period substantially equal to the duration of insulin action. Such previous boluses may include extended boluses that were completed during the previous time period and/or immediate boluses (e.g., meal boluses or correction boluses) that were delivered during the previous time period.

If any previous bolus had been delivered during the previous time period, the method may then calculate 420 the insulin on board value(s) from those previous bolus(es). For a previous bolus that was an immediate bolus delivered during the previous time period, the previous bolus IOB value may be calculated as follows:

$$IOB = (V \times (1 - T_e / DIA)) \quad (5)$$

where V is the volume delivered by the immediate bolus, DIA is the duration of insulin action, and $T_e$ is the elapsed time since the immediate bolus was delivered (e.g., measured from the time the bolus was completed).

For a previous bolus that was an extended bolus completed during the previous time period, an IOB value may be calculated for the portion of the extended bolus that occurred during the previous time period. As described above, this completed portion of the extended bolus may be represented by a series of immediate bolus portions delivered during that previous time period. This IOB value may thus be calculated by calculating and summing the IOB values for the series of immediate bolus portions representing that portion of the extended bolus, for example, as described above.

The previous bolus IOB values may be calculated separately for correction boluses and meal bolus resulting in a separate correction bolus IOB value and meal bolus IOB value. If multiple correction boluses or meal boluses were given during the previous time period, the correction bolus IOB value or meal bolus IOB value may be calculated by summing the IOB values for the correction boluses or meal boluses respectively. The calculation of insulin on board may also take into account insulin on board from basal doses of insulin being delivered.

A suggested bolus may then be calculated 422 using the calculated IOB values. The suggested bolus may be calculated, for example, by calculating a suggested correction bolus component and a suggested meal bolus component and by subtracting one or more of the calculated IOB values to determine an effective suggested correction bolus component and an effective suggested meal bolus component.

A correction bolus may be calculated based on a current blood glucose level, a target blood glucose level or range, and an insulin correction factor. The target blood glucose level and correction factor may be retrieved from the user data stored in the system or received from user input. The current blood glucose level may be obtained, for example, by testing and inputting the test data into the system or by using continuous glucose monitoring (CGM) integrated into the insulin delivery system.

According to one example, a correction bolus may be calculated as follows:

$$CB = (CBG - TBG) / CF \quad (6)$$

where CBG is the current blood glucose level (e.g., in mg/dl), TBG is a target blood glucose level (e.g., in mg/dl), and CF is CF is the correction factor. In some cases, the correction bolus may be determined to be 0 if the current blood glucose level does not exceed a target blood glucose correction threshold. In some cases, the correction bolus may be calculated to be a negative number to provide a reverse correction if the current blood glucose level is below a target blood glucose level or range.

The effective suggested correction bolus may be calculated by subtracting one or more of the calculated IOB values described above. In one embodiment, the effective suggested correction bolus may be calculated by subtracting both correction IOB values and meal IOB values including extended bolus IOB values. The effective suggested correction bolus may also be adjusted by a user.

A meal bolus may be calculated based on the carbohydrate intake and an insulin-to-carbohydrate ratio. The insulin-to-carb ratio may be a user-specified data stored in the system or entered by the user. The carb intake value may be entered by the user or selected from a library of predetermined carb intake values. According to one example, a meal bolus may be calculated as follows:

$$MB = (C / IC) \quad (7)$$

where C is digestible carbohydrates from the carb intake and IC is the I/C ratio. Digestible carbohydrates may be determined by subtracting an amount (e.g., grams) of fiber from an amount (e.g., grams) of carbohydrates.

The effective suggested meal bolus may be calculated by subtracting one or more calculated IOB values. In one embodiment, the effective suggested meal bolus may be calculated by subtracting a correction bolus IOB value but not a meal bolus IOB value. If the suggested bolus includes both a meal bolus portion and a correction bolus portion, for example, the meal bolus IOB value may be subtracted from the correction bolus portion up to the point where the correction bolus would become 0, but the meal bolus IOB value would not be subtracted from the meal bolus portion.

If the suggested bolus includes only a meal bolus portion (i.e., a carb intake and the current blood glucose is in the target range or below the correction threshold), the suggested bolus may be calculated as follows:

$$SB = MB - IOB_c \quad (8)$$

where MB is the meal bolus and $IOB_c$ is the total correction IOB value.

If the suggested bolus includes only a correction bolus portion (i.e., the current blood glucose is above the target range or the correction threshold but no carb intake), the suggested bolus may be calculated as follows:

$$SB = CB - IOB_c - IOB_m \quad (9)$$

where CB is the correction bolus, $IOB_c$ is the total correction IOB value, and $IOB_m$ is the total meal IOB value including both immediate meal bolus IOB values and extended meal IOB values.

If the suggested bolus includes both a meal bolus portion and a correction bolus portion, the suggested bolus may be calculated as follows:

$$SB = RCB - IOB_c + MB \quad (10)$$

where RCB is a reduced correction bolus (i.e., the correction bolus reduced by the meal IOB value), $IOB_c$ is the total correction IOB value, and MB is the meal bolus volume. The reduced correction bolus may be calculated as follows:

$$RCB = CB - IOB_m \text{ if } IOB_m < CB \quad (11)$$

$$RCB = 0 \text{ if } IOB_m \geq CB \quad (12)$$

where CB is the correction bolus and $IOB_m$ is the total meal IOB value including both immediate meal bolus IOB values and extended meal IOB values. Other methods for calculating a suggested bolus may also be used.

The IOB calculation system and method may also be used to calculate an extended bolus IOB value during an extended bolus dose for suggesting other doses of insulin. For example, the IOB calculation system and method may be used to calculate an extended bolus IOB for suggesting a temporary basal rate provided over a programmed period of time and/or a suspension of insulin for a period of time. The IOB from an extended bolus may impact a temporary basal rate, the suspension of insulin, and an extended bolus as well as a correction bolus or a food bolus.

The extended bolus IOB value may also be calculated (e.g., together with other IOB values) to provide the user with insulin on board information. The insulin on board information may include the extended bolus IOB value, IOB values from other previous boluses (e.g., immediate meal and correction boluses), and/or a total IOB value. This insulin on board information may be displayed or otherwise provided to the user. A user may want to know insulin on board information if the user is about to engage in any activity affecting blood glucose levels, for example, if the user is about to exercise or eat a meal. If there is insulin on board before exercise, the user may want to eat to avoid low blood glucose levels. If there is insulin on board before eating, a user may avoid an additional unnecessary infusion of insulin. A user may also want to know insulin on board information if the user is about to suspend insulin delivery, for example, by disconnecting from an insulin delivery system.

The method of calculating an IOB as described herein may also be used for calculating IOB from a temporary basal rate and specifically from increased temporary basal rates. In this variation of the method, the amount of basal insulin above a "normal" basal rate may be used to calculate the IOB by calculating an IOB value for the completed portion of the temporary basal rate and by calculating an IOB value for the scheduled portion of the temporary basal rate. Thus, the amount of basal insulin above a "normal" basal rate may be considered to be a form of an extended bolus.

In other variations of the method described herein, a carbohydrate glycemic index may be used to indicate whether or not and how much the IOB should be considered with carbs that are known to absorb more slowly (e.g., a lower glycemic index). The carbohydrate glycemic index may be captured, for example, via a user prompt at the time of carb consumption.

Figure 5:
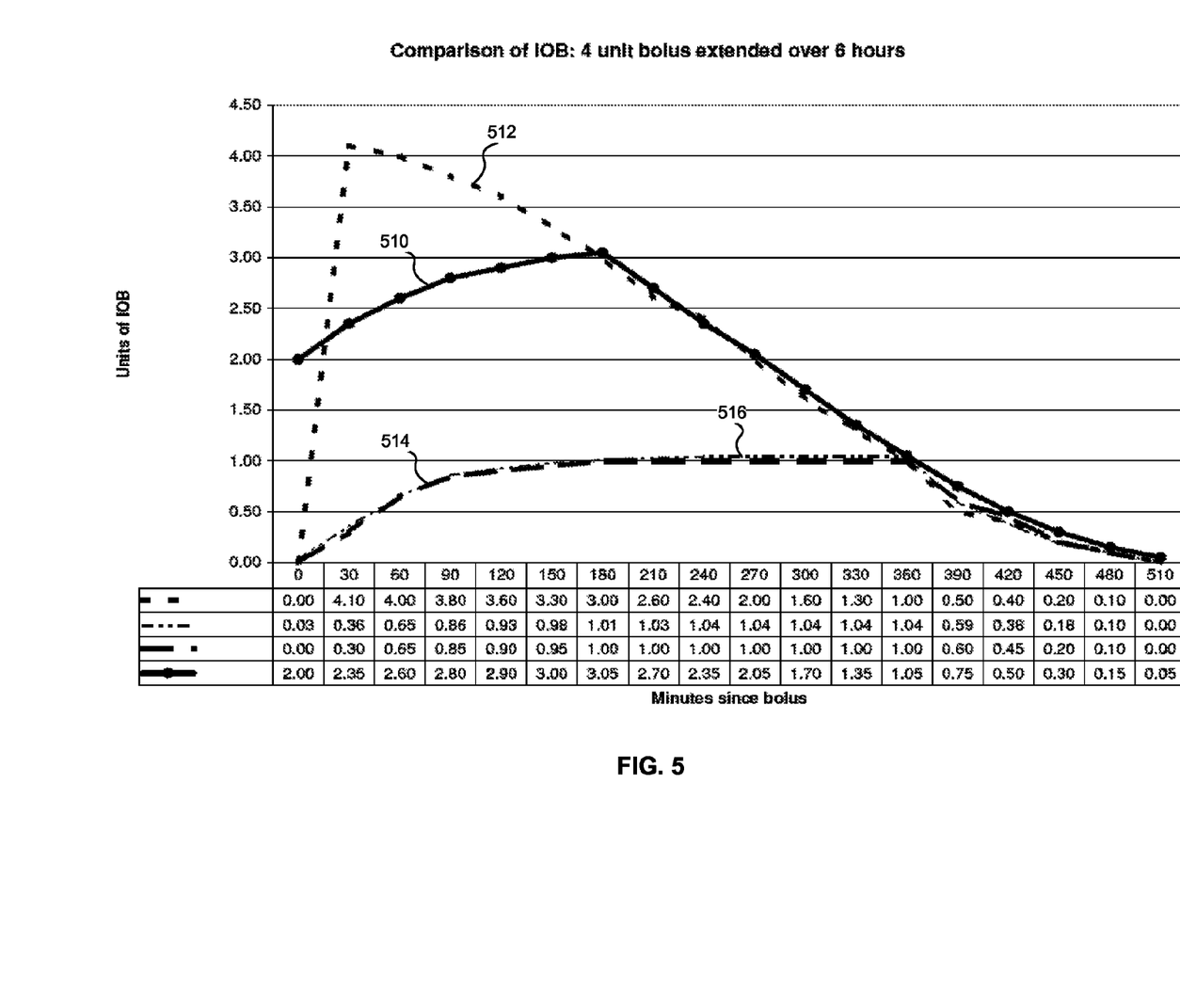
FIG. 5 is a graph illustrating one example of insulin on board calculated for an extended bolus using different methods.
Figure 6:
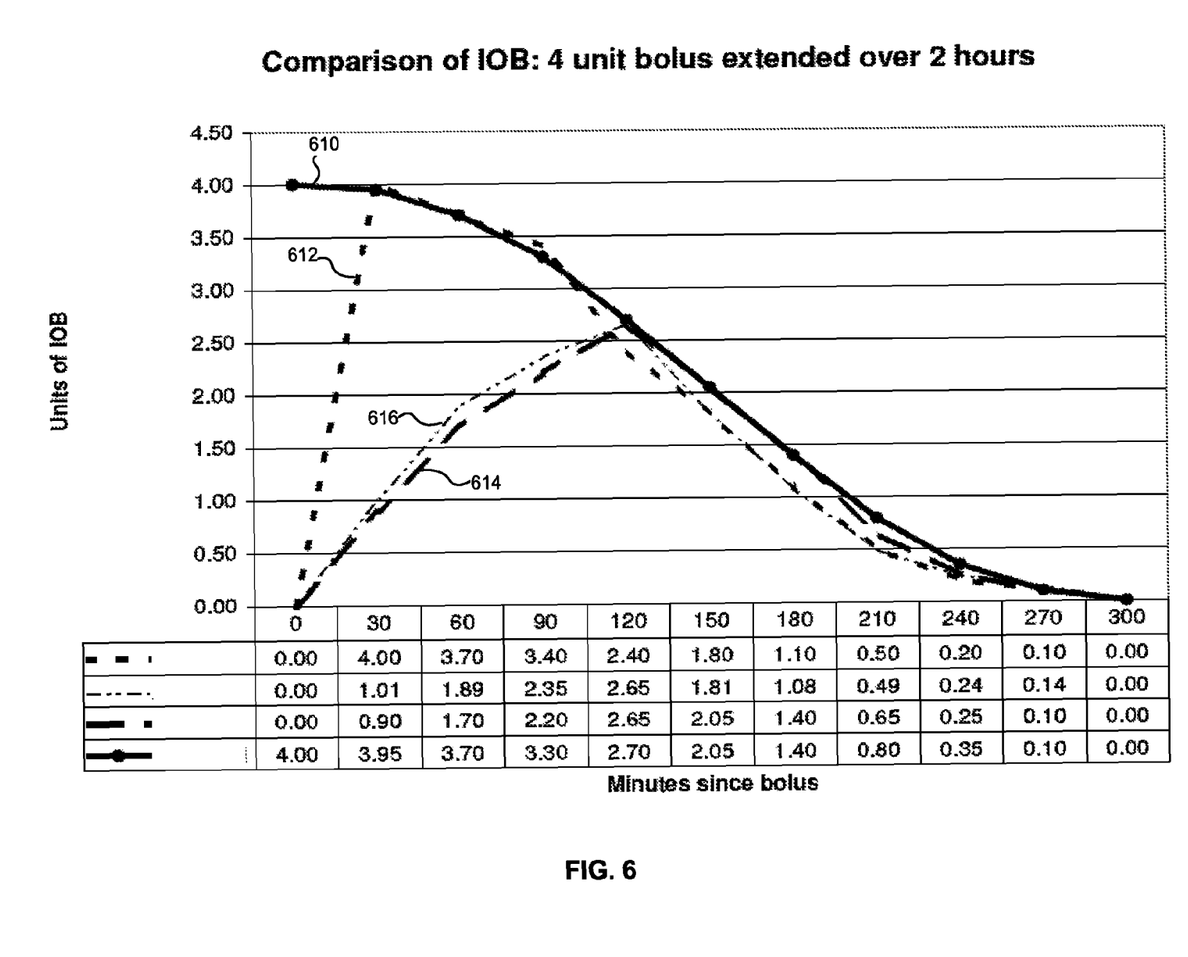
FIG. 6 is a graph illustrating another example of insulin on board calculated for an extended bolus dose using different methods.

FIGS. 5 and 6 illustrate examples of an extended bolus IOB calculation, consistent with embodiments of the present invention, compared to other IOB calculations calculated using other techniques during an extended bolus. According to both examples, the blood glucose level is 100 mg/dl and is within a target range, the carbohydrate intake is 60 g, the extended bolus dose is 4 units, and the duration of insulin action is 3 hours. The duration of the extension of the bolus is different in each of the examples shown in FIGS. 5 and 6.

According to the example in FIG. 5, the duration of the extension of the bolus is 100% over 6 hours, which is greater than the duration of insulin action. The extended bolus IOB curve 510 represents the extended bolus IOB value calculated according to the method described above. As shown, at the start of the extended bolus, the extended bolus IOB value is 2 units. At this time there is no completed portion and the scheduled IOB portion is calculated as 2 units to be delivered over the subsequent 3 hour period. Because the duration of the extended bolus is longer than the duration of insulin action, the scheduled IOB portion of the extended bolus IOB value remains at 2 units until the time remaining is less than the duration of insulin action. The extended bolus IOB value increases as the completed IOB portion increases until the time remaining is less than the duration of insulin action (i.e., after 3 hours or 180 minutes). When the time remaining in the extended bolus is less than the duration of insulin action, the extended bolus IOB value decreases because the scheduled IOB portion decreases.

The extended bolus IOB value calculated consistent with embodiments of the present invention may have advantages over other approaches to calculating the IOB during an extended bolus because such other approaches are either too aggressive or too conservative. The IOB curve 512 shows a more conservative approach, which has much higher IOB values at the beginning of the extended bolus. This conservative approach considers all future extended bolus to be "on board." Such an approach may result in suggested bolus calculations that are too low at the beginning of the extended bolus, which may cause insufficient insulin delivery and high blood glucose.

The IOB curves 514, 516 show more aggressive approaches, which have much lower IOB values throughout most of the extended bolus. These approaches only consider the insulin that is truly "on board" at the time. Such approaches may result in suggested bolus calculations that are too high, which may cause excessive insulin delivery and low blood glucose. The extended bolus IOB values calculated consistent with embodiments of the present invention may thus prevent low blood glucose caused by a suggested bolus that is too aggressive and may prevent excessively high blood glucose caused by a suggested bolus that is too conservative.

According to the example in FIG. 6, the duration of the extension is 100% over 2 hours, which is less than the duration of insulin action. The extended bolus IOB curve 610 represents the extended bolus IOB value calculated according to the method consistent with embodiments of the present invention. Because the duration of the extension is less than the duration of insulin action, the scheduled IOB portion (and the extended bolus IOB value) is calculated to be the full 4 units at the start of the extended bolus. The extended bolus IOB value is then reduced as a function of the scheduled IOB portion of the IOB value being reduced. The IOB curves 612, 614, 616 again show other approaches to calculating the extended bolus IOB compared to the method described herein. Accordingly, an extended bolus IOB calculation system and method, consistent with embodiments described herein, allows a more reliable determination of insulin on board and calculation of a suggested bolus.

Although exemplary embodiments described herein involve insulin delivery, the concepts of the extended bolus IOB calculation system and method described above may be applied to other types of drugs or medicines that may be delivered as an extended bolus by an infusion pump to treat or prevent a disease or illness. For such drugs the duration of action may be determined as the period of time in which the drug remains active in the body to treat a particular condition. If the duration of action for the particular drug or medicine can be determined, the system and method described above may be used to calculate a bolus on board (BOB) value for that particular drug or medicine. The calculation of an extended bolus BOB value may take into account the amount of the drug or medicine that is currently on board up to that point in time and the amount of drug or medicine scheduled to be delivered during a subsequent time period substantially equal to the duration of action for that particular drug, for example, using the techniques described above.

Other types of drugs or medicines that can be delivered by an infusion pump include, but are not limited to, antibiotics, nutritional fluids, total parenteral nutrition or TPN, analgesics, morphine, hormones or hormonal drugs, gene therapy drugs, anticoagulants, analgesics, cardiovascular medications, AZT or chemotherapeutics. Other types of medical conditions that might be treated include, but are not limited to, diabetes, cardiovascular disease, pain, chronic pain, cancer, AIDS, neurological diseases, Alzheimer's Disease, ALS, Hepatitis, Parkinson's Disease or spasticity.

Consistent with one embodiment, a method is provided for calculating insulin on board (IOB) for an extended bolus being delivered by an insulin infusion device. The method includes determining a completed IOB value representing an amount of insulin on board from a completed portion of the extended bolus that has been completed within a previous time period substantially equal to a duration of insulin action; determining a scheduled IOB value representing an amount of insulin scheduled to be delivered during a scheduled portion of the extended bolus within a subsequent time period substantially equal to the duration of insulin action; and adding the completed IOB value to the scheduled IOB value to produce an extended bolus IOB value.

Consistent with another embodiment, a method is provided for calculating insulin on board (IOB) for a user of an insulin infusion device. The method includes determining if the insulin infusion device is currently delivering an extended bolus; if the insulin infusion device is currently delivering at least one extended bolus, calculating at least one extended bolus insulin on board (IOB) value that takes into account an amount of insulin currently on board up to that point in time from the extended bolus and an amount of insulin scheduled to be delivered from the extended bolus within a subsequent time period substantially equal to a duration of insulin action; determining if the insulin infusion device has delivered any previous bolus within a previous time period substantially equal to the duration of insulin action; if the insulin infusion device has delivered at least one previous bolus within the previous time period, calculating at least one previous insulin on board (IOB) value for the at least one previous bolus; and adding the at least one extended bolus IOB value and the at least one previous IOB value to produce a total IOB value.

Consistent with a further embodiment, a method is provided for determining a suggested bolus of insulin to be delivered by an insulin infusion device. The method includes: determining if the insulin infusion device is currently delivering an extended bolus; if the insulin infusion device is currently delivering at least one extended bolus, calculating at least one extended bolus insulin on board (JOB) value that takes into account an amount of insulin currently on board up to that point in time from the extended bolus and an amount of insulin scheduled to be delivered from the extended bolus within a subsequent time period substantially equal to a duration of insulin action; determining if the insulin infusion device has delivered any previous bolus within a previous time period substantially equal to the duration of insulin action; if the insulin infusion device has delivered at least one previous bolus within the previous time period, calculating at least one previous insulin on board (JOB) value for the at least one previous bolus; and calculating a suggested bolus using at least one calculated IOB value selected from the group consisting of the at least one extended bolus IOB value and the at least one previous IOB value.

Consistent with yet another embodiment, a machine-readable medium includes contents that cause a processor to perform the method of calculating insulin on board for an extended bolus as described above.

Consistent with yet another embodiment, a method is provided for calculating bolus includes: determining a completed BOB value representing an amount of the drug on board from a completed portion of the extended bolus that has been completed within a previous time period substantially equal to a duration of action of the drug; determining a scheduled BOB value representing an amount of the drug scheduled to be delivered during a scheduled portion of the extended bolus within a subsequent time period substantially equal to the duration of action; and adding the completed BOB value to the scheduled BOB value to produce an extended bolus BOB value.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A computer implemented method of calculating insulin on board (IOB) for a user of an insulin infusion device, the method, performed via one or more processors, comprising:
   determining if the insulin infusion device is currently delivering an extended bolus;
   if the insulin infusion device is currently delivering at least one extended bolus, calculating at least one extended bolus insulin on board (IOB) value that takes into account an amount of insulin currently on board up to that point in time from the extended bolus and an amount of insulin scheduled to be delivered from the extended bolus within a subsequent time period substantially equal to a duration of insulin action;
   determining if the insulin infusion device has delivered any previous bolus within a previous time period substantially equal to the duration of insulin action;
   if the insulin infusion device has delivered at least one previous bolus within the previous time period, calculating at least one previous insulin on board (IOB) value for the at least one previous bolus; and
   adding the at least one extended bolus IOB value and the at least one previous IOB value to produce a total IOB value.

2. The method of claim 1 wherein calculating the at least one previous IOB value includes calculating a meal IOB value representing insulin currently on board from a previous meal bolus given within the previous time period and a correction IOB value representing insulin currently on board from a previous correction bolus given within the previous time period.

3. The method of claim 1 wherein calculating the extended bolus IOB value comprises:
   determining a completed IOB value representing an amount of insulin on board from a completed portion of the extended bolus that has been completed within a previous time period substantially equal to a duration of insulin action;
   determining a scheduled IOB value representing an amount of insulin scheduled to be delivered during a scheduled portion of the extended bolus within a subsequent time period substantially equal to the duration of insulin action; and
   adding the completed IOB value to the scheduled IOB value to produce the extended bolus IOB value.

4. A computer implemented method of determining a suggested bolus of insulin to be delivered by an insulin infusion device, the method, performed via one or more processors, comprising:

determining if the insulin infusion device is currently delivering an extended bolus;

if the insulin infusion device is currently delivering at least one extended bolus, calculating at least one extended bolus insulin on board (IOB) value that takes into account an amount of insulin currently on board up to that point in time from the extended bolus and an amount of insulin scheduled to be delivered from the extended bolus within a subsequent time period substantially equal to a duration of insulin action;

determining if the insulin infusion device has delivered any previous bolus within a previous time period substantially equal to the duration of insulin action;

if the insulin infusion device has delivered at least one previous bolus within the previous time period, calculating at least one previous insulin on board (IOB) value for the at least one previous bolus; and calculating a suggested bolus using at least one calculated IOB value selected from the group consisting of the at least one extended bolus IOB value and the at least one previous IOB value.

5. The method of claim 4 wherein calculating the extended bolus IOB value comprises:

determining a completed IOB value representing an amount of insulin on board from a completed portion of the extended bolus that has been completed within a previous time period substantially equal to a duration of insulin action;

determining a scheduled IOB value representing an amount of insulin scheduled to be delivered during a scheduled portion of the extended bolus within a subsequent time period substantially equal to the duration of insulin action; and adding the completed IOB value to the scheduled IOB value to produce the extended bolus IOB value.

6. The method of claim 4 wherein calculating a suggested bolus dose includes:

calculating a meal bolus portion representing an amount of insulin to cover a carbohydrate intake;

calculating a correction bolus portion representing an amount of insulin to correct blood glucose to within a target blood glucose range; and adding the carbohydrate bolus and the correction bolus and subtracting the at least one calculated IOB value.

7. The method of claim 6 wherein the suggested bolus is an extended bolus.

8. The method of claim 4 wherein calculating the at least one previous IOB value includes calculating a meal IOB value representing insulin currently on board from a previous meal bolus given within the previous time period and a correction IOB value representing insulin currently on board from a previous correction bolus given within the previous time period.

9. The method of claim 8 wherein calculating a suggested bolus dose includes calculating a meal bolus representing an amount of insulin to cover a carbohydrate intake and subtracting the correction IOB value.

10. The method of claim 8 wherein calculating a suggested bolus dose includes calculating a correction bolus representing an amount of insulin to correct blood glucose to within a target blood glucose range and subtracting the at least one extended bolus IOB value, the meal IOB value, and the correction IOB value.

11. A non-transitory machine-readable medium whose contents cause a processor to perform a method of calculating insulin on board (IOB) for a user of an insulin infusion device, the method comprising:

determining if the insulin infusion device is currently delivering an extended bolus;

if the insulin infusion device is currently delivering at least one extended bolus, calculating at least one extended bolus insulin on board (IOB) value that takes into account an amount of insulin currently on board up to that point in time from the extended bolus and an amount of insulin scheduled to be delivered from the extended bolus within a subsequent time period substantially equal to a duration of insulin action;

determining if the insulin infusion device has delivered any previous bolus within a previous time period substantially equal to the duration of insulin action;

if the insulin infusion device has delivered at least one previous bolus within the previous time period, calculating at least one previous insulin on board (IOB) value for the at least one previous bolus; and adding the at least one extended bolus IOB value and the at least one previous IOB value to produce a total IOB value.

12. The non-transitory machine-readable medium of claim 11 wherein calculating the at least one previous IOB value includes calculating a meal IOB value representing insulin currently on board from a previous meal bolus given within the previous time period and a correction IOB value representing insulin currently on board from a previous correction bolus given within the previous time period.

13. The non-transitory machine-readable medium of claim 11 wherein calculating the extended bolus IOB value comprises:

determining a completed IOB value representing an amount of insulin on board from a completed portion of the extended bolus that has been completed within a previous time period substantially equal to a duration of insulin action;

determining a scheduled IOB value representing an amount of insulin scheduled to be delivered during a scheduled portion of the extended bolus within a subsequent time period substantially equal to the duration of insulin action; and adding the completed IOB value to the scheduled IOB value to produce the extended bolus IOB value.

14. A non-transitory machine-readable medium whose contents cause a processor to perform a method of determining a suggested bolus of insulin to be delivered by an insulin infusion device, the method comprising:

determining if the insulin infusion device is currently delivering an extended bolus;

if the insulin infusion device is currently delivering at least one extended bolus, calculating at least one extended bolus insulin on board (IOB) value that takes into account an amount of insulin currently on board up to that point in time from the extended bolus and an amount of insulin scheduled to be delivered from the extended bolus within a subsequent time period substantially equal to a duration of insulin action;

determining if the insulin infusion device has delivered any previous bolus within a previous time period substantially equal to the duration of insulin action;

if the insulin infusion device has delivered at least one previous bolus within the previous time period, calculating at least one previous insulin on board (IOB) value for the at least one previous bolus; and calculating a suggested bolus using at least one calculated IOB value selected from the group consisting of the at least one extended bolus IOB value and the at least one previous IOB value.

15. The non-transitory machine-readable medium of claim 14 wherein calculating the extended bolus IOB value comprises:
- determining a completed IOB value representing an amount of insulin on board from a completed portion of the extended bolus that has been completed within a previous time period substantially equal to a duration of insulin action;
- determining a scheduled IOB value representing an amount of insulin scheduled to be delivered during a scheduled portion of the extended bolus within a subsequent time period substantially equal to the duration of insulin action; and
- adding the completed IOB value to the scheduled IOB value to produce the extended bolus IOB value.

16. The non-transitory machine-readable medium of claim 14 wherein calculating a suggested bolus dose includes:
- calculating a meal bolus portion representing an amount of insulin to cover a carbohydrate intake;
- calculating a correction bolus portion representing an amount of insulin to correct blood glucose to within a target blood glucose range; and
- adding the carbohydrate bolus and the correction bolus and subtracting the at least one calculated IOB value.

17. The non-transitory machine-readable medium of claim 16 wherein the suggested bolus is an extended bolus.

18. The non-transitory machine-readable medium of claim 14 wherein calculating the at least one previous IOB value includes calculating a meal IOB value representing insulin currently on board from a previous meal bolus given within the previous time period and a correction IOB value representing insulin currently on board from a previous correction bolus given within the previous time period.

19. The non-transitory machine-readable medium of claim 18 wherein calculating a suggested bolus dose includes calculating a meal bolus representing an amount of insulin to cover a carbohydrate intake and subtracting the correction IOB value.

20. The non-transitory machine-readable medium of claim 18 wherein calculating a suggested bolus dose includes calculating a correction bolus representing an amount of insulin to correct blood glucose to within a target blood glucose range and subtracting the at least one extended bolus IOB value, the meal IOB value, and the correction IOB value.

* * * * *